United States Patent [19]

Karger et al.

[11] Patent Number: 5,085,757

[45] Date of Patent: Feb. 4, 1992

[54] INTEGRATED TEMPERATURE CONTROL/ALIGNMENT SYSTEM FOR HIGH PERFORMANCE CAPILLARY ELECTROPHORETIC APPARATUS

[75] Inventors: Barry L. Karger, Newton; Robert J. Nelson, Boston, both of Mass.

[73] Assignee: Northeastern University, Boston, Mass.

[21] Appl. No.: 399,600

[22] Filed: Aug. 28, 1989

Related U.S. Application Data

[63] Continuation-in-part of Ser. No. 125,539, Nov. 25, 1987, Pat. No. 4,898,658.

[51] Int. Cl.⁵ .................. G01N 27/26; B01D 57/02
[52] U.S. Cl. .................. 204/299 R; 204/180.1; 204/183.3
[58] Field of Search ............... 204/299 R, 180.1, 183.3

[56] References Cited

U.S. PATENT DOCUMENTS

| | | | |
|---|---|---|---|
| 3,677,930 | 7/1972 | Meshbane et al. | 204/299 |
| 3,948,753 | 4/1976 | Arlinger | 204/299 |
| 4,608,146 | 8/1986 | Penaluna | 204/299 R |
| 4,624,768 | 11/1986 | Yoshida et al. | 204/299 |
| 4,675,300 | 6/1987 | Zare et al. | 436/172 |
| 4,898,658 | 2/1990 | Karger et al. | 204/299 R |
| 4,985,129 | 1/1991 | Burd | 204/299 R |

FOREIGN PATENT DOCUMENTS

| | | |
|---|---|---|
| 339780 | 11/1989 | European Pat. Off. |
| 2328785 | 5/1977 | France |
| 53-3893 | 1/1978 | Japan |

OTHER PUBLICATIONS

Patent Abstracts of Japan, vol. 9, No. 273 (P-401) (1996) Oct. 30, 1985, and JP-A-60 119456 (Shimazu Seisakusho K.K.) Jun. 26, 1985.

*Primary Examiner*—John Niebling
*Assistant Examiner*—John S. Starsiak, Jr.
*Attorney, Agent, or Firm*—Weingarten, Schurgin, Gagnebin & Hayes

[57] ABSTRACT

An integrated temperature control/alignment system for use with a high performance capillary electrophoretic apparatus comprises a complementary pair of capillary column mounting plates formed from an electrically insulative, high thermal conductivity material for mounting a capillary column. The first mounting plate includes a well having a predetermined circumference, first and second grooves contiguous with the well and ports formed in the grooves and extending through the plate. The second mounting plate includes a plug configured for insertion in the well and ports aligned with the ports of the first mounting plate. Respective ends of the capillary column are seated and locked in the grooves to preposition the capillary column with respect to the ports. Capillary columns of varying lengths may be mounted within the mounting plates by coiling the intermediate portion thereof within the well to increase or decrease the working length of the column in predetermined increments, depending upon the particular application. Optical coupling elements are disposed in the ports to couple sampling and reference radiation to and from the mounted capillary column. The temperature of substantially the entire capillary column is controlled or regulated by at least one thermopile disposed in thermal contact with one of the mounting plates. A thermistor may be thermally coupled to the capillary column or one of the mounting plates to provide feedback signals to operate the thermopile to maintain the capillary column at a predetermined electrophoretic operating temperature.

11 Claims, 6 Drawing Sheets

_Fig. 16_

INTEGRATED TEMPERATURE CONTROL/ALIGNMENT SYSTEM FOR HIGH PERFORMANCE CAPILLARY ELECTROPHORETIC APPARATUS

RELATED APPLICATION

This application is a continuation-in-part of application Ser. No. 07/125,539, now U.S. Pat. No. 4,898,658 filed Nov. 25, 1987, entitled INTEGRATED TEMPERATURE CONTROL/ALIGNMENT SYSTEM FOR HIGH PERFORMANCE CAPILLARY ELECTROPHORETIC APPARATUS, incorporated herein by reference.

FIELD OF THE INVENTION

This invention relates generally to electrophoretic apparatus, and more particularly to a temperature control/alignment system integrated with a high performance capillary electrophoretic apparatus.

BACKGROUND OF THE INVENTION

Capillary electrophoresis is a technique for analyzing and/or purifying a wide variety of biochemical substances or analytes such as proteins, nucleic acids, carbohydrates, hormones and vitamins. In particular, electrophoresis is an extremely efficacious and powerful means for the identification and/or separation of analytes based upon ultra-small volume samples. In general, electrophoresis is a phenomenon that involves the migration of charged particles or analytes through a conducting liquid solution under the influence of an applied voltage.

The basic capillary electrophoretic apparatus consists of a capillary column having the ends thereof positioned in reservoirs containing electrodes. A conducting liquid or buffer solution disposed in the reservoirs and the capillary column comprises the electrophoretic conductive circuit.

An analyte is injected into the appropriate end of the capillary column and a voltage applied across the electrodes. The applied voltage causes the analyte to migrate electrophoretically through the capillary column past a prepositioned on-column detection device to generate an electropherogram, a graphical representation of the analyte.

Electrophoresis may be conducted in "open" or "gel" capillary columns. Open capillary electrophoresis can be conducted either with or without electroosmosis which involves bulk solvent migration under the influence of the applied voltage as a result of the charged condition of the inner wall of the capillary column. Gel capillary electrophoresis, in which the interior channel of the capillary column is filled with a suitable gel, provides the potential for different modes of separation based upon size of the analytes.

In either open or gel capillary electrophoresis, however, the applied voltage is a primary factor affecting the migration of the analyte. Therefore, the term electromigration as used herein encompasses either or both forms of voltage induced analyte movement.

An effective high performance capillary electrophoretic system provides high resolution, high sensitivity, short run times, on-line monitoring or detection of the analyte, and reproducible performance. One practical way of enhancing the performance of a capillary electrophoretic apparatus is by the application of high applied voltages. Another is to utilize shortened capillary columns. Both of these means of enhancing the effectiveness of the electrophoretic apparatus, however, have heretofore been limited due to the Joule heat generated in the capillary column during the electrokinetic separation operation which adversely affects electrophoretic separations.

The applied voltage causes a current flow in the buffer solution of the electrophoretic apparatus that is generally defined by Ohm's Law. The current flow through the capillary column generates Joule heat or thermal energy in the capillary column. Increasing the applied voltage increases the current flow and the resulting increased power raises the amount of Joule heat generated, which is generally an adverse condition. Similarly, shortening the length of the capillary column decreases the capillary column resistance, thereby causing an increase in current flow for a given applied voltage with the concomitant increase in Joule heating.

Column temperature influences most of the important physical and chemical parameters involved in high performance capillary electrophoresis. In particular, column temperature directly affects electrophoretic separation since there is a variation in mobility of about 2%/°C. For any given electrophoretic separation, there is generally a preferred column temperature for optimal separation conditions. A column temperature deviation of only 1° C. may affect the migration rate, thereby adversely impacting on separation reproducibility. Other adverse effects that may result from column temperature deviations include reduced separation efficiency, sample decomposition, and the inability to maintain the desired chemical equilibria.

Joule heat generated within the capillary column, if not efficiently controlled and/or dissipated to the ambient environment, causes a temperature buildup within the column. The temperature buildup detrimentally affects the electrophoretic separation by inducing variations in column resistance, which affects current flow, and concomitantly Joule heating, in the column FIG. 18 illustrates the variations in column current with time, with a constant applied voltage, for various methods of cooling a capillary electrophoretic column.

Curves 1 and 2, respectively, illustrate column cooling by natural convection and forced air convection with a fan. An examination of these curves reveals a noticeable variation in column current with time. Point A indicates the effect of the operation of an air conditioner in the laboratory, and shows that both natural convection and forced air cooling are susceptible to changes in the laboratory environment. Curve 3 illustrates cooling of the capillary column by means of a solid state cooling device according to the present invention. The solid state cooling device provides: (1) isolation of capillary column from ambient environmental conditions and (2) precise control of the temperature of the capillary column. FIG. 18 also graphically illustrates the fact that, although each electrophoretic separation was conducted under the same operating conditions, there was a significant deviation in column current flow, and hence column operating temperature (57° C., 33° C., 24° C., respectively, based upon the corresponding column current flow and the mobility rate of 2%/°C.), among the electrophoretic operations due to the different methods of cooling.

An optimized high performance capillary electrophoretic apparatus provides statistically reproducible results for equivalent analytes, with minimum band broadening of the output. Preferably, the apparatus is operated at high applied voltages to provide high speed, efficiency and resolution of separations. An optimized high performance capillary electrophoretic apparatus must include a temperature control system that maximizes reproducibility of column resistance and minimizes any detrimental thermal effects on separation. The temperature control system, in addition to effectively maintaining a constant column temperature, should have the capability to vary the column temperature depending upon the particular application.

For example, it may be important to vary column temperature to manipulate chemical equilibria such as metal chelation and micelle partitioning. Electrophoretic separations below ambient temperature have been shown to be useful in minimizing proteolysis or sample decomposition. Electrophoretic separation of oligonucleotides, in contrast, have been improved by injecting at 60° C. where the species adopts a random coil configuration.

Prior art attempts to cool the capillary electrophoretic apparatus have involved natural and forced convection cooling. Due to disadvantages associated with many cooling solvents, e.g., low cooling capacity, flamability, toxicity, and/or high costs, water has generally been used as the cooling element in prior art electrophoretic convection cooling systems. In additional to being high capacity devices, requiring two to four liters of water, water-cooled devices suffer a marked degradation in cooling performance, about 20 to 40 percent, at temperatures approaching four degrees centigrade. And while water-cooled devices provide an improvement over air-convection devices in controlling column temperature, water-cooled devices are severely limited in capability to rapidly vary the column temperature for different applications, and a relatively expensive. In addition, a water coolant has a sufficient degree of electrical conductivity to interfere with the electrophoretic separation process.

Another limiting aspect of prior art capillary electrophoretic apparatus was due to the fact that the structural configuration of temperature regulating systems severely hindered temperature control in the detection zone. A lack of temperature control can lead to non-reproducible results in migration rates and separation. Likewise, for accurate collection of a given species in micropreparative applications, the column length between the detection zone and the collection point should be minimized, and this column length should have similar temperature characteristics to the separation region prior to the detection zone in order to predict accurately when a peak leaves the column.

Moreover, reproducible results in signal-to-noise ratio were difficult to achieve in prior art capillary electrophoretic apparatus due to the cumbersome and time consuming effort required to properly align and lock the capillary column with respect to the prepositioned detection device. Improper alignment of or failure to lock the capillary column in a predetermined position leads to the generation of variable noise due to vibration effects, which can lead to poor detection limits.

SUMMARY OF THE INVENTION

The present invention surmounts the inherent disadvantages of the prior art by providing an integrated temperature control/alignment system for a high performance capillary electrophoretic apparatus. The integrated temperature control/alignment system provides a means for regulating and/or varying the temperature of the capillary column, over substantially the entire working length thereof, to a predetermined operating temperature by dissipating or in some instances augmenting, in order to operate at elevated column temperatures, the Joule heat generated by current flow through the capillary column.

Temperature regulation of the capillary column is effected by controlling a secondary current flow through a thermoelectric device, thereby regulating heat transfer away from or into the capillary column. An effective means of temperature regulation permits a higher voltage to be applied across the capillary column of given diameter than if the system were not present, with the accompanying increase in apparatus performance. The structural configuration of the integrated temperature control/alignment system also permits thermoelectric temperature regulation over the on-column detection zone of the capillary column.

In addition, the integrated temperature control/alignment system provides a means for mounting the capillary column as a constituent of the electrophoretic apparatus. The structural configuration of the integrated temperature control/alignment system facilitates the precise alignment of the detection "windows" of the capillary column with the detection openings of the integrated temperature control/alignment system for on-column detection. The structural configuration of the integrated temperature control/alignment system coacts with the capillary column to lock the capillary column therein in a predetermined aligned position with respect to the on-column detection device. The locking feature of the present invention effectively eliminates adverse vibratory effects which would have affected the output while the alignment feature ensures reproducible results.

One exemplary embodiment of the integrated temperature control/alignment system according to the present invention comprises a pair of capillary column mounting plates for mounting the capillary column as a constituent of the electrophoretic apparatus, a pair of secondary support plates, a pair of thermoelectric plates and external heat sink plates.

The capillary column mounting plates are formed from an electrically insulating material and each plate has a lengthwise groove sized to snugly seat the capillary column. With the capillary column mounting plates disposed in contacting relation with the capillary column sandwiched therebetween in the grooves, the capillary column is effectively locked into position within the integrated temperature control/alignment system.

A detection slit and a detection hole are formed through the respective capillary column mounting plates so as to be substantially centered about the lengthwise groove thereof. The capillary column is seated within the grooves of the capillary column mounting plates so that the detection windows thereof are precisely aligned with the detection slit and hole, respectively. This ensures that the capillary column is mounted as a constituent of the electrophoretic apparatus in alignment with the prepositioned on-column detection device.

The secondary support plates are fabricated and utilized to facilitate heat transfer between the encapsulated capillary column and the thermoelectric plates as well as to provide for increased structural strength of the integrated temperature control/alignment system. Each secondary support plate has a detection slot formed therethrough. The secondary support plates are disposed in contact with the exterior facing surfaces of the respective capillary column mounting plates in such manner that the detection slots are aligned with the detection slit and hole, respectively.

Thermoelectric plates are disposed in contact with the exterior facing surfaces of the respective secondary support plates. Each thermoelectric plate includes one or more thermoelectric conducting circuits or thermopiles functioning to regulate heat transfer with the capillary column. During typical electrophoretic operating conditions, the thermoelectric plates function to provide thermoelectric cooling for the capillary column sandwiched within the integrated temperature control/alignment system by transferring Joule heat produced within the capillary column through the respective plates of the integrated temperature control/alignment system to the ambient environment.

Controlling the direction and magnitude of the current flow through the thermoelectric conducting circuits permits thermoelectric regulation of both the direction and rate of heat transfer with the capillary column, and the ambient environment as required. The direction of heat transfer may be such as to either dissipate or augment the Joule heat generated within the capillary column, such that the temperature of the capillary column is precisely controlled. Each thermoelectric plate can include a detection passageway aligned with the respective detection slot, the detection passageway being required when the thermoelectric plate is one unitary thermopile, that is a single thermoelectric conducting circuit.

External heat sink plates are disposed in contact with respective thermoelectric plates to transfer Joule heat away from the capillary column when the system operates to provide thermoelectric cooling of the capillary column. The external heat sink plates act to transfer the thermal energy or Joule heat of the higher temperature surface of the thermoelectric plates to the external ambient environment. Heat transfer to the ambient environment may be effected by radiative, convective, and/or conductive heat transfer from the external heat sink plates. Detection apertures can be formed through the external heat sink plates so as to be aligned with the detection slots or the detection passageways, depending upon the particular configuration of the thermoelectric plates.

Another exemplary embodiment of the integrated temperature control/alignment system consists of a module that is configured to include means for mounting capillary columns of different length while concomitantly providing solid state cooling over substantially the entire working length thereof and means for decoupling the detection device from the module. The module is configured for slidable insertion and removal from an electrophoretic container that provides interfacing with associated electrophoretic electronics, detection equipment, power supply, and ancillary cooling equipment such as heat sinks and/or forced air convection gear. One or more thermopiles are disposed in combination with the module to control and/or vary the temperature thereof.

The module comprises first and second mounting plate members formed from an insulative, highly thermal conductive material such as alumina and configured to be mated together in combination. The first and second mounting plate members, in combination with the associated thermopiles, provide solid state temperature control for the capillary column disposed therewith.

The first mounting plate member includes a well and first and second grooves extending from diametrically opposed points of the well to an edge of the plate. Ports are formed in respective grooves and extending through the first plate member for respective elements of the sample and reference optical coupling means. The first and second grooves are dimensioned for snugly seating the respective ends of a capillary column. The well is defined by a circumferential wall having a predetermined circumference. The intermediate portion of the mounted capillary column abuts against the circumferential wall.

The well provides the capability to accommodate capillary columns of different length such that the module may be utilized to provide varying capillary column working lengths. The intermediate portion of polymer coated microcapillary columns may be coiled a predetermined number of turns within the well to provide a predetermined column working length that is variable in increments. The inherent resilience of such columns causes the coiled intermediate portion to abut against the circumferential wall.

The second mounting plate member is formed to complement the first mounting plate member and includes a plug and ports extending therethrough in registration with the ports of the first mounting plate member. The plug is configured to be disposed within the well with the second mounting block member mated in combination with the first mounting block member.

Sample and reference optical coupling means such as optical fibers may be mounted in corresponding ports of the first and second mounting block members. The sample and reference radiation coupling means provide an optical interface between the module and the radiation coupling means mounted in the container.

BRIEF DESCRIPTION OF THE DRAWINGS

A more complete understanding of the present invention and the attendant advantages and features thereof will be more readily understood by reference to the following detailed description when considered in conjunction with the accompanying drawings wherein:

FIG. 18 is a performance graph contrasting prior art methods of cooling and the solid state cooling system of the present invention.

DETAILED DESCRIPTION OF THE PREFERRED EMBODIMENTS

Figure 1:
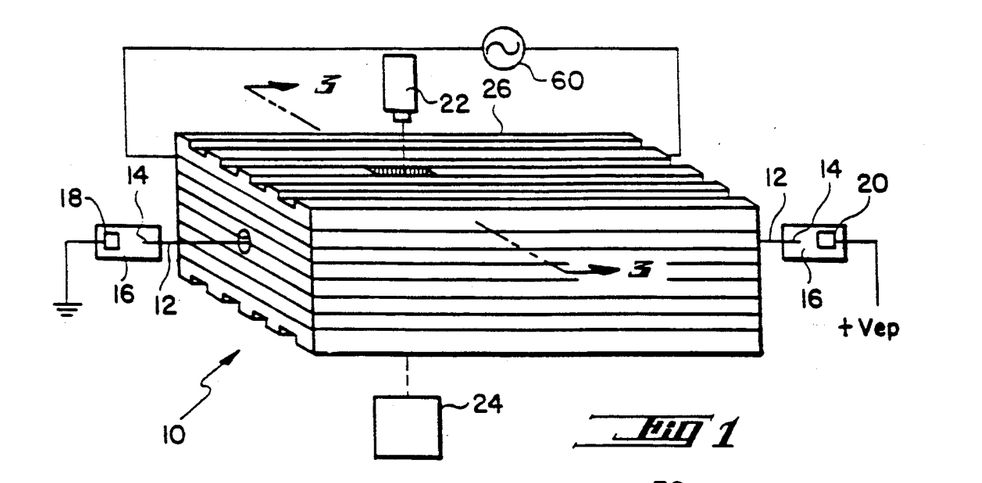
FIG. 1 is a schematic representation of one embodiment of a high performance capillary electrophoretic apparatus utilizing an integrated temperature control/alignment system according to the present invention.

Referring now to the drawings wherein like reference numerals designate corresponding or similar elements throughout the several views, there is shown generally in FIG. 1 a high performance capillary electrophoretic (HPCE) apparatus 10 according to the present invention. The basic capillary electrophoretic apparatus 10 comprises a capillary tube or column 12 having ends 14, 14 disposed in buffer solution reservoirs 16, 16.

Electrodes 18, 20 electrically connect the buffer solution reservoirs 16, 16 to apply a voltage, Vep, across the electrodes 18, 20, respectively, thereby providing the motive force for electrophoretic migration of an analyte. The capillary column 12 is mounted as a constituent of the HPCE apparatus 10 by means of an integrated temperature control/alignment system 26, as described hereinbelow in greater detail.

An on-column detection device 22, 24 is externally prepositioned with respect to the HPCE apparatus 10 for on-column detection of the electromigrating analyte. For purposes of illustration only, the on-column detection device 22, 24 is herein described as a UV radiation source 22 which focuses UV radiation to pass through the detection openings of the integrated temperature control/alignment system 26 and the detection windows of the capillary column 12 for ensuing detection by a detection means 24.

The capillary column 12 is a thin-walled, hollow tube, preferably formed of a low specific heat, non-conducting material such as fused silica. The capillary column 12 may be either "open" or "gel." Typical gels for the interior of the capillary column 12 include polyacrylamide or agarose.

The capillary column 12 typically has a length in the range of 10 cm to 100 cm, an internal diameter (I.D.) in the range of 25 microns to 200 microns, and an outer diameter (O.D.) in the range of 125 microns to 350 microns, depending upon the I.D. of the capillary column 12. Capillary columns having an I.D. in the range of about 50 to about 100 microns provide improved detectability, ease of handling and column loading.

Since a quartz based fused silica capillary columns 12 having the above-disclosed dimensions are relatively fragile, the strength and flexibility of the capillary column 12 are generally increased by applying an external protective coating of a polymer such as polyimide to the capillary column 12.

Figures 2, 3, 4, 5:
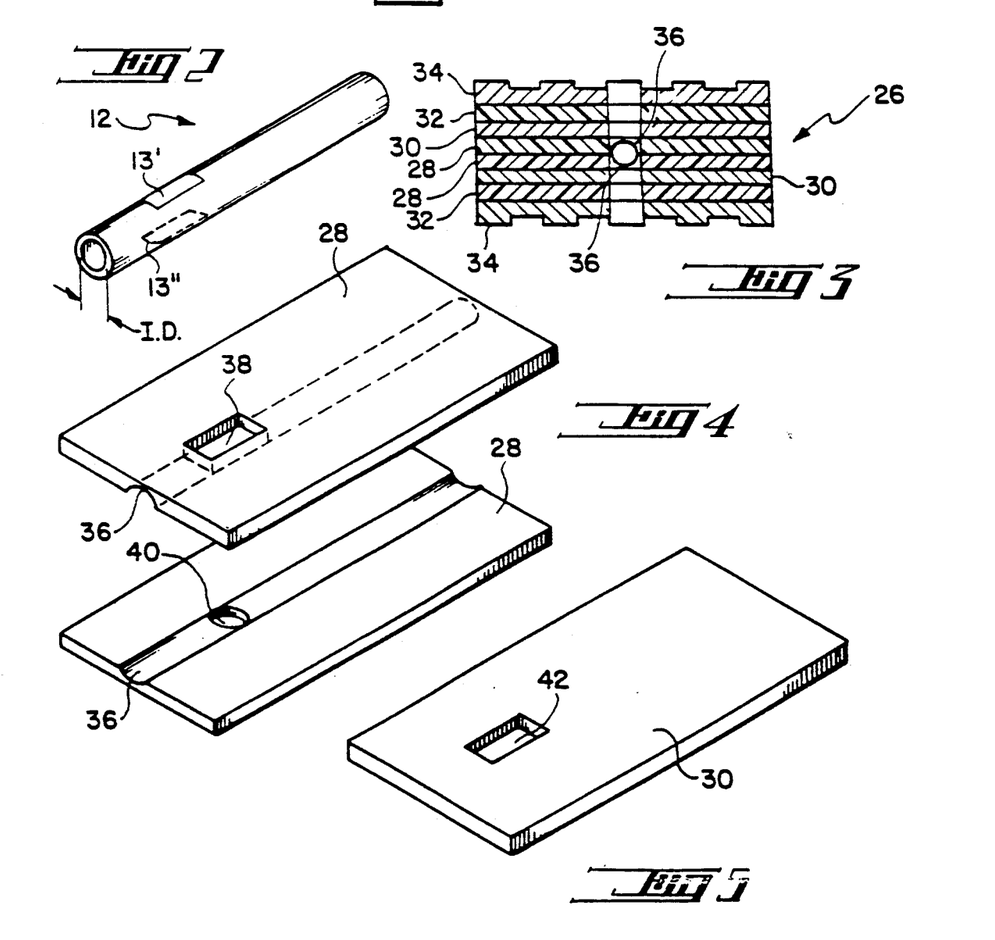
FIG. 2 is a perspective view of a capillary column illustrating the opposed detection windows thereof.
FIG. 3 is a cross sectional view taken along line 3-3 of FIG. 1 of one embodiment of the integrated temperature control system of the present invention.
FIG. 4 is a perspective view of the capillary column mounting plates according to the present invention.
FIG. 5 is a perspective view of a secondary support plate according to the present invention.

The polyimide coating, however, would interfere with the operation of the on-column detection device 22, 24. Therefore, the coating of the capillary column 12 is typically modified to include detection "windows" which permit measurement or sensing of the electromigrating analyte during passage through the interior of the capillary column 12. As shown in FIG. 2, the polyimide coating is selectively removed at opposed locations on the capillary column 12 at the predetermined position to create first and second detection windows 13, 13, spaced approximately 180 degrees from one another. A device for efficiently, selectively and easily removing the polyimide coating is described in copending application Ser. No. 07/342,989, filed Apr. 24, 1989, entitled WINDOW BURNER FOR POLYMER COATED CAPILLARY COLUMNS.

Alternatively, a 360 degree peripheral band of the polyimide coating may be removed at the predetermined position on the capillary column 12. One of ordinary skill in the art will appreciate that "windows" is used herein in a generic sense to refer to a modified segment or segments of the capillary column 12 at the predetermined position wherein some form of measurement/sensing means is provided access into and out of the capillary column 12 to detect the electromigrating analyte. To simplify the ensuing discussion, the on-column detection device 22, 24 is exemplarily described as a UV radiation source and UV detection means.

The irradiated volume within the capillary column 12 between the detection "windows" defines the electrophoretic detection zone. The detection radiation generated by the on-column detection device 22, 24 is focused to traverse the detection zone of the capillary column 12.

During the generation of electropherograms the ends 14, 14 of the capillary column 12 are disposed in the buffer solution reservoirs 16, 16 in such a manner as to be in fluidic contact with the buffer solution. Prior to insertion of the ends 14, 14 in the respective buffer solution reservoirs 16, 16, the interior of the capillary column 12 is filled with the gel/buffer solution and the analyte is electrophoretically injected into the appropriate end 14 thereof. The buffer solution acts as the electrically conductive medium for the electrophoretic circuit.

The electrophoretic conducting circuit for the HPCE apparatus 10 is completed by inserting the first electrode 18 in one buffer solution reservoir 16 and the second electrode 20 in the other buffer solution reservoir 16. The electrodes 18, 20 are preferably formed of a chemically inert material such as platinum to preclude a degrading reaction between the electrodes 18, 20 and the buffer solution of the reservoirs 16, 16.

Figure 11:
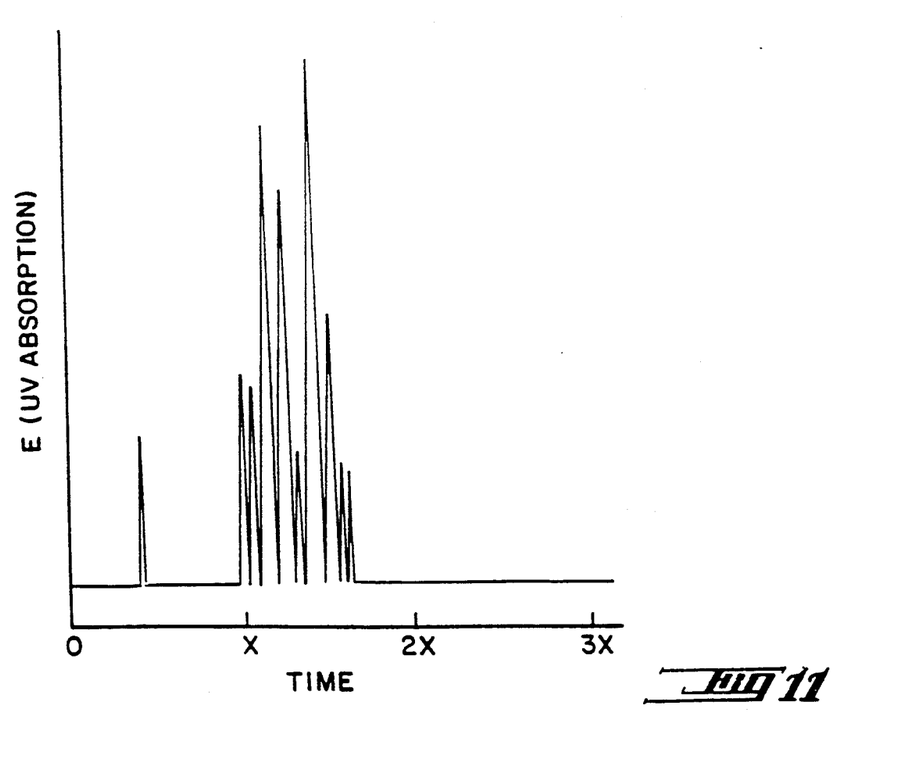
FIG. 11 is an exemplary electropherogram generated by means of an HPCE apparatus.

During electrophoresis, the voltage, Vep, is applied across the HPCE apparatus 10 to generate a current in the electrophoretic circuit. The applied voltage, $V_{ep}$, causes the electromigration of the analyte injected into the appropriate end 14 of the capillary column 12 through the capillary column 12 to the other end 14. Passage of the analyte through the capillary tube 12 past the prepositioned on-column detection device 22, 24 causes the generation of an electropherogram which is a graphical time display of the quanta of detected radiation. The passage of the electromigrating analyte through the detection zone causes the monochromatic radiation traversing the capillary column 12 to be scattered and/or absorbed. A representative example of an electropherogram derived by means of the HPCE apparatus 10 is shown in FIG. 11.

The exemplary on-column detection device 22, 24 comprises a means for generating a monochromatic beam of UV radiation 22 and focusing the beam to pass substantially orthogonally through the first detection window 13 of the capillary column 12. One such monochromatic radiation generating means 22 having utility in the HPCE apparatus 10 of the present invention is an UV deuterium lamp producing ultraviolet radiation in the 190–380 nanometer range. By means of a suitable lens/filter arrangement the monochromatic beam of ultraviolet radiation, of predetermined wavelength, is focused to radiate through the first detection window 13 substantially orthogonal thereto.

The monochromatic radiation traverses the capillary column 12 and the medium, e.g., gel, buffer solution and/or analyte solution, disposed between the first and second detection windows 13, 13 and exits therefrom through the second detection window 13. The exiting radiation is focused upon a suitable detection means 24 such as a photomultiplier which is responsive to changes in radiation intensity. When the analyte in the capillary column 12 electromigrates through the detection zone between the first and second detection windows 13, 13 the monochromatic radiation is scattered and/or absorbed, thereby generating an electropherogram as shown in FIG. 11.

Other usable monochromatic radiation may be produced by IR and visible radiation sources. Fluorescence is another detection technique usable for on-column monitoring of the electrophoretically migrating analyte. It will be appreciated that the on-column detection technique is not limited to the generation and detection of radiation. Other detection techniques having utility for on-column detection include conductivity and electrochemical measurements/sensing. The common denominator for all on-column detection techniques is access to the capillary column in some predetermined manner.

One embodiment of the integrated temperature control/alignment system 26 for mounting the capillary column 12 as a constituent of the HPCE apparatus 10 is shown in greater detail in the end view of FIG. 3. The temperature control/alignment system 26 of FIG. 3 is a multi-layered structure consisting of a pair of capillary column mounting members or plates 28, 28 for mounting the capillary column 12 as part of the HPCE apparatus 10, a pair of secondary support plates 30, 30, a pair of thermoelectric plates 32, 32, and external heat sink plates 34, 34.

The capillary column mounting plates 28, 28 illustrated in FIG. 4 are preferably fabricated from an electrically insulating material, preferably a ceramic-type material having good dielectric characteristics and possessing a reasonable coefficient of thermal conductivity. One suitable ceramic material is alumina, $Al_2O_3$, which has a thermal conductivity of approximately 36 W m$^{-1}$ °K$^{-1}$ at 293° K. It will be appreciated, however, that the capillary column mounting plates 28, 28 may be fabricated metallic conducting materials for some applications. Each capillary column mounting plate 28 has a lengthwise groove 36 formed in an interior facing surface thereof.

The groove 36 has a maximum width which is approximately equal to the O.D. of the capillary column 12 and a depth which is approximately equal to one half of the O.D. of the capillary column 12. The dimensioning of the grooves 36 ensures that the capillary column 12 is snugly seated or physically engaged therein, and further that when the interior facing surfaces of the capillary column mounting plates 28, 28 are disposed in contacting relationship, the capillary column 12 is locked or sandwiched therebetween in an immotile condition.

A detection slit 38 is formed through the upper capillary column mounting plate 28 in such a manner as to be substantially centered about the groove 36 thereof and a detection hole 40 is formed through the lower capillary column mounting plate 28 in such a manner as to be substantially centered about the groove 36 thereof, as shown in FIG. 4. The detection slit 38 has a length in the range of about 2 mm or less and a width in the range approximately equal to or less than the I.D. of the capillary column 12. The detection hole 40 has a diameter in the range of about 2 mm or less. When the upper and lower capillary column mounting plates 28, 28 are disposed in contacting relationship, as shown in FIG. 3, the detection slit 38 is aligned with the detection hole 40.

The detection slit 38 and the detection hole 40 are formed through the upper and lower capillary column mounting plates 28, 28 in such a manner that when the capillary column 12 is seated in the opposed grooves 36 of the capillary support strips 28, 28, the detection slit 38 can be readily aligned with the first detection window 13 and the detection hole 40 can be readily aligned with the second detection window 13. The structural configuration of the capillary column mounting plates 28, 28 thus facilitates the alignment of the capillary column 12 with respect to the prepositioned on-column detection device 22, 24, thereby ensuring the reproducibility of results as well as consistency therebetween.

With the grooved faces of the capillary column mounting plates 28, 28 secured together in a contacting relationship, the capillary column 12 is locked in the opposed grooves 36 thereof. A thermally conductive paste may be used to ensure a tight, thermally conducting pathway between the capillary column 12 and the capillary column mounting plates 28, 28.

Disposed in contact with the exterior facing surfaces of the capillary column mounting plates 28, 28 are the interior facing surfaces of the secondary support plates 30, 30, as shown in FIG. 5. The secondary support plates 30, 30 are typically fabricated as metal members or plates which provide a good thermally conductive medium between the capillary column mounting plates 28, 28 and the thermoelectric plates 32, 32 to facilitate the transfer of Joule heat between the capillary column 12 and the thermoelectric plates 32, 32.

In addition, the secondary support plates 30, 30 provide increased structural strength for the integrated temperature control/alignment system 26. Representative metals having utility in forming the secondary support plates 30, 30 for use in the present invention include copper, which has a thermal conductivity of approximately 398 W m$^{-1}$ °K$^{-1}$ at 300° K, and aluminum, which has a thermal conductivity of approximately 237 W m$^{-1}$ °K$^{-1}$ at 293° K.

As shown in FIG. 5, a detection slot 42 is formed in each of the secondary support plates 30, 30 in such manner that when the integrated temperature control/alignment system 26 is assembled in final configuration with the capillary column 12 sandwiched therein, the detection slots 42 of the secondary support plates 30, 30 are aligned with the detection slit 38 and the detection hole 40, respectively, of the capillary column mounting plates 28, 28.

The interior facing surfaces of the thermoelectric plates 32, 32 are disposed in contact with the exterior facing surfaces of the secondary support plates 30, 30, respectively. Each thermoelectric plate 32 comprises at least one electrically conducting circuit or thermopile utilizing the Peltier effect to thermoelectrically regulate the electrophoretic operating temperature, $T_{cc}$, of the capillary column 12 by the controlling the transfer of thermal energy to or from the capillary column 12.

The Peltier effect describes a phenomenon wherein an electric current flowing through the junction between two dissimilar metals or conducting elements, i.e., a thermocouple, can absorb or generate thermal energy at the junction depending upon the direction of the current flow. The rate of heat transfer at the junction is directly proportional to the magnitude of the current flowing through the junction. The thermal energy transfer rate is thus directly controllable by regulating the magnitude of the current flowing through the thermoelectric circuit. In addition, by controlling the direction of current flow in the thermoelectric circuit, the thermoelectric effect exerted on the capillary column 12 is regulated to provide either thermoelectric cooling or thermoelectric heating of the capillary column 12.

To simplify the disclosure, the operation of the thermoelectric plates 32, 32 will be described in terms of providing thermoelectric cooling for the capillary column 12, i.e., the thermoelectric plates 32, 32 act to transfer the Joule heat generated in the capillary column 12 to the heat sink plates 34, 34 via the capillary column mounting plates 28, 28, the secondary support plates 30, 30 and the thermoelectric plates 32, 32, since electrophoretic operations typically are concerned with the dissipation of Joule heat generated within the capillary column 12. The thermoelectric cooling provided by the thermoelectric plates 32, 32 thus effectively cools the secondary support plates 30, 30, and the capillary column mounting plates 28, 28 and concomitantly lowers the electrophoretic operating temperature, $T_{cc}$, of the capillary column 12 to a predetermined operating temperature.

Figures 6, 7:
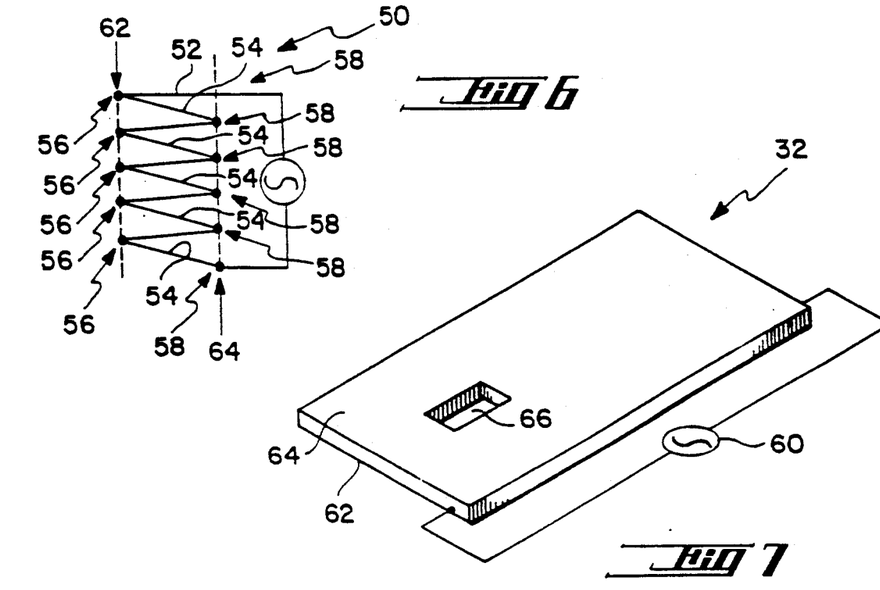
FIG. 6 is a schematic representation of a thermopile.
FIG. 7 is a perspective view of one embodiment of a thermoelectric plate according to the present invention.

By connecting a plurality of thermocouples in series to an external current source, a thermopile 50 is formed, as schematically illustrated in FIG. 6. The thermopile 50 is comprised of a first plurality of conducting elements 52 and a second plurality of conducting elements 54 joined as shown in FIG. 6 to form a first plurality of dissimilar junctions 56 and a second plurality of dissimilar junctions 58 electrically connected to a variable current source 60. Bismuth telluride is a representative compound used in forming the conducting elements of the thermopile 50, with the first and second plurality of conducting elements 52, 54 formed by doping the bismuth telluride with "p" and "n" type metals, respectively.

The first plurality of dissimilar junctions 56 are disposed in first planes 62 to form the interior facing surfaces of the first and second thermoelectric plates 32, 32 and the second plurality of dissimilar junctions 58 are disposed in second planes 64 to form the exterior facing surfaces of the first and second thermoelectric plates 32, 32. The junctions may be maintained in such a relationship permanently, as for example by fixing the thermocouples in an epoxy infrastructure of suitable electrically insulating material.

Proper selection of the magnitude and direction of the current generated by the variable current source 60 flowing in the thermopile circuit 50 maintains the first plurality of dissimilar junctions 56 at a temperature, $T_L$, while the second plurality of dissimilar junctions 58 are maintained at a temperature, $T_H$, that is, the first plurality of dissimilar junctions 56 cool down while the second plurality of dissimilar junctions 58 heat up.

The thermoelectric plates 32, 32 are configured such that during electrophoresis the temperature $T_L$ maintained at the first plurality of dissimilar junctions 56 is less than the predetermined electrophoretic operating temperature, $T_{cc}$, at which the capillary column 12 is operated during electrophoresis. This ensures that a heat transfer potential is maintained between the capillary column 12 and the interior facing surfaces of the thermoelectric plates 32,32 such that Joule heat generated in the capillary column 12 during electrophoresis is transferred away from the capillary column 12. The value of $T_L$, and hence the rate of thermal energy transfer or the thermoelectric cooling effect of the thermoelectric plates 32, 32, is regulated by varying the output of the current source 60 such that the operating temperature, $T_{cc}$, of the capillary column 12 is precisely maintained. One or more thermopiles 50 as described hereinabove are arranged to function singly or in combination as the thermoelectric plates 32, 32 utilized in the integrated temperature control/alignment system 26 according to the present invention.

The embodiment of the thermoelectric plate 32 shown in FIG. 7 is a unitary thermopile 50, that is a single thermoelectric circuit, which has the first plurality of dissimilar junctions 56 disposed so as to form the interior facing surface 62 in contact with the exterior facing surface of the respective secondary support plate 30 while the second plurality of dissimilar junctions 58 are disposed to form the exterior facing surface 64 in contact with the interior facing surface of the respective heat sink plate 34. Since the embodiment of the thermoelectric plate 32 of FIG. 7 is a unitary thermopile 50, each thermoelectric plate 32 must be modified to include a detection passageway 66 aligned with the respective detection slot 42 of the corresponding secondary support plate 30 for on-column detection of the electrophoretically migrating analyte.

Figures 8, 9:
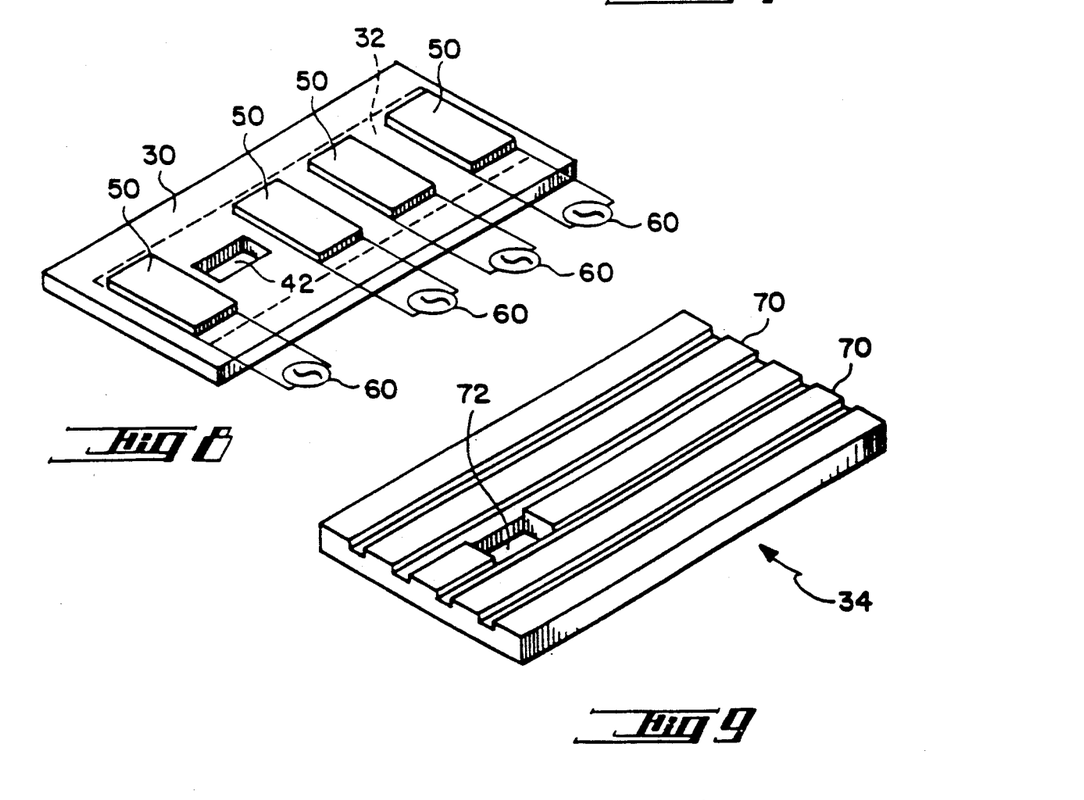
FIG. 8 is a perspective view of an alternative embodiment of the thermoelectric plate according to the present invention.
FIG. 9 is a perspective view of one embodiment of a heat sink plate for use with the present invention.

FIG. 8 illustrates another embodiment of the thermoelectric plate 32 of the present invention wherein each thermoelectric plate 32 consists of a plurality of individual thermopiles 50, four being shown in FIG. 8, which act in combination to transfer thermal energy from the secondary support plate 32 to the heat sink plate (not shown). As illustrated in FIG. 8 each thermopile 50 has its own current source 60. The individual current sources 60 may be gang controlled to regulate the temperature $T_L$. It will be appreciated that the individual thermopiles 50 of each thermoelectric plate 32 can be disposed to form, in effect, a detection passageway 66. This is accomplished by affixing the individual thermopiles 50 to the exterior facing surfaces of the corresponding secondary support plates 30, 30 so as not to overlap or obstruct the detection slots 42, 42.

One embodiment of the heat sink plate 34 of the present invention is depicted in FIG. 9. Each heat sink plate 34 of the embodiment of FIG. 9 includes a plurality of radiating fins 70 for externally dissipating the thermal energy transferred to the heat sink plate 34 by radiative and/or convective heat exchange between the radiating fins 70 and the ambient environment where the HPCE apparatus 10 is set up. The convective heat exchange of the heat sink plate 34 may be either passive or active.

Operating the heat sink plate 34 for active convective heat exchange requires the utilization of any conventionally known means for forcing a greater fluid volume over the surface area of the heat sink plate 34 to increase the rate of convective heat exchange between the heat sink plate 34 and the fluid. Each heat sink plate 34 also includes a detection aperture 72 aligned with the respective detection passageway 66 of the thermoelectric plate 32 (for the embodiment disclosed by FIG. 7) or the detection slot 42 of the respective secondary support plate 30 (for the embodiment disclosed by FIG. 8).

Figure 10:
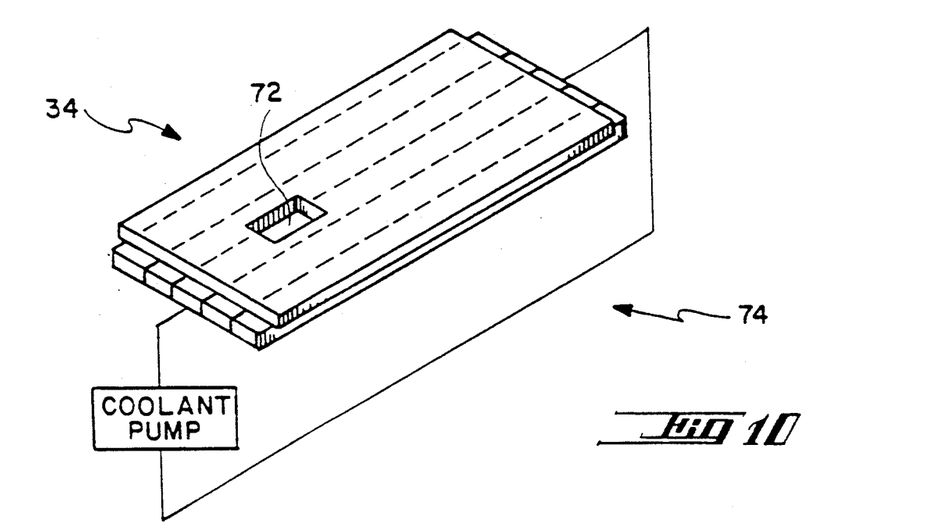
FIG. 10 is a perspective view of an alternative embodiment of a heat sink plate for use with the present invention.

Alternatively, as shown in FIG. 10 the heat sink plate 34 can be primarily cooled by conduction by means of a cooling system 74 which circulates a cooling fluid for heat exchange through the heat sink plate 34. Such an embodiment is effective where the capillary column 12 of the HPCE apparatus 10 is to be operated at predetermined operating temperatures $T_{cc}$ which require large quanta of Joule heat to be transferred to the ambient environment. The circulating cooling fluid ensures that the necessary heat transfer potential is maintained for effective Joule heat transfer between the thermoelectric plates 32, 32 and the heat sink plates 34, 34. This embodiment likewise includes the detection aperture 72 as described hereinabove.

The integrated temperature control/alignment system 26 described hereinabove provides an improved means for regulating heat transfer between the capillary column 12 and the ambient environment. The direction and rate of heat transfer with respect to the capillary column 12 is regulated by the thermoelectric effect provided by means of the magnitude and direction of the electric current flowing in the thermoelectric plates 32, 32. Regulation of the direction and rate of heat transfer regulates or controls the electrophoretic operating temperature, $T_{cc}$, of the capillary column 12. By utilizing the integrated temperature control/alignment system 26 to thermoelectrically cool the capillary column 12 as described in the preceding paragraphs, the HPCE apparatus 10 according to the present invention is operable at higher $V_{ep}$s, which results in the generation of higher resolution electropherograms and/or analyte separation in shorter run times. By utilizing the integrated temperature control/alignment system 26 according to the present invention, reproducible high quality results are obtainable down to electrophoretic operating temperature, $T_{cc}$, of $-20°$ C.

It is to be understood that the integrated temperature control/alignment system 26 of the present invention can also be utilized to thermoelectrically heat the capillary column 12, that is, to augment the Joule heat generated within the capillary column 12 to raise the electrophoretic operating temperature, $T_{cc}$. When the integrated temperature control/alignment system 26 is operated to thermoelectrically heat the capillary column 12, the heat sink plates 34, 34 need not be included as elements of the integrated temperature control/alignment system 26.

It will further be appreciated that the structural configuration of the integrated temperature control/alignment system 26 as described hereinabove provides thermoelectric regulation of the temperature proximal the detection zone of the capillary column 12. This likewise increases the accuracy and reproducibility of the electrophoretic separation. Moreover, the disclosed structural configuration of the integrated temperature control/alignment 26 system facilitates the proper alignment of the windows of the capillary column 12 with respect to the prepositioned on-column detection device 22, 24, i.e., in the detection zone.

Other embodiments based upon the integrated temperature/control alignment system are possible in light of the above teachings. For example, another embodiment of the integrated temperature control/alignment system comprises only the capillary column mounting plates and the thermoelectric plates as described hereinabove. Another embodiment of the integrated temperature control/alignment system comprises only the thermoelectric plates, the interior facing surfaces of each thermoelectric plate having formed therein grooves and a detection slit and a detection hole, respectively, as described hereinabove for seating and locking the capillary column in alignment with the prepositioned on-column detection device.

Although the embodiments of the integrated temperature control/alignment system have been described hereinabove in terms of a plate configuration, it is to be understood that the present invention is not to be limited by the terminology "plate". The integrated temperature control/alignment system can also be formed as series of individual concentric tubes, as functionally described hereinabove, coaxially disposed about the capillary column. It will be appreciated that for this embodiment no groove is necessary in the capillary column support tube in that the configuration of the tube itself performs the seating and locking function.

Another embodiment of an integrated temperature control/alignment module 26' for a HPCE apparatus 10 is illustrated in FIGS. 12-16 and includes features that permit the module 26' to be utilized under a variety of separation conditions. The integrated temperature control/alignment module 26' includes means for mounting capillary columns of different length without changing the basic structural configuration of the module 26' while concomitantly providing solid state cooling over substantially the entire working length thereof, and means for decoupling the on-column detection device 22, 24 from the module 26', as described hereinbelow in greater detail.

Figure 12:
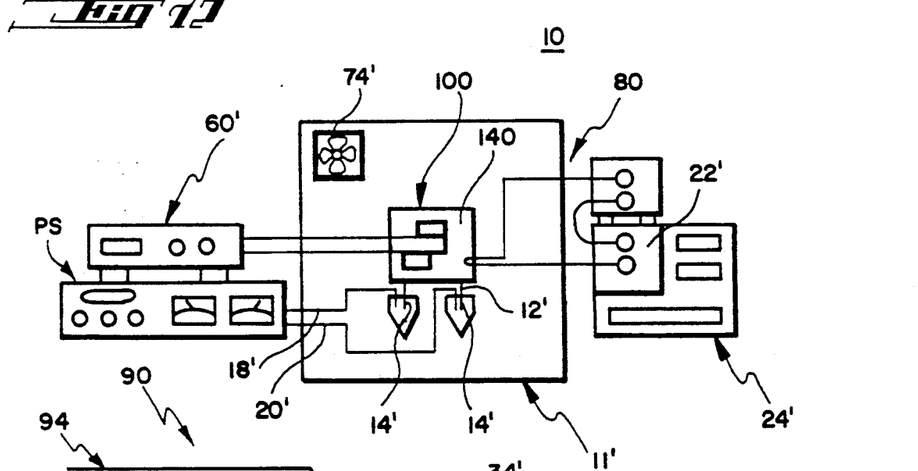
FIG. 12 is schematic representation of another embodiment of a high performance capillary electrophoretic apparatus according to the present invention.

A schematic diagram of the HPCE apparatus 10 is illustrated in FIG. 12. The apparatus 10 includes a light-tight insulative container 11', a capillary column 12' having ends 14', 14' disposed in buffer solution reservoirs 16', 16'. Electrodes 18', 20' are disposed in the reservoirs 16', 16' and electrically connected to a power supply PS to apply a voltage $V_{ep}$ across the electrodes 18', 20'. The capillary column 12' is mounted within the container 11' of the HPCE apparatus 10 by means of the integrated temperature control/alignment module 26', described hereinbelow in greater detail, which is disposed within an insulated holder 100.

The exemplary on-column detection device consists of a UV radiation source 22', a detection means 24' and radiation coupling means 80 for coupling radiation from the source 22' to the capillary column 12' and from the capillary column 12 to the detection means 24'. The capillary column 12' is mounted within the integrated temperature control/alignment module 26'. The module 26' includes complementary first and second mounting plate members 28', 29' and one or more thermopiles 50' mounted in combination therewith for controlling and/or varying the temperature of the module 26'. A thermally conductive substance, for example a high temperature thermally conductive paste (Omega Engineering, Inc., Stamford, Conn.) or ethylene glycol, may be utilized to enhance the thermal contact between the module 26' and the thermopiles 50'. The thermopiles 50 are electrically connected to a thermoelectric temperature controller 60'. External heat sink plates 34' (FIG. 13) and a cooling system 74', such as a fan, may be utilized to effect heat removal from the thermopiles 50'.

The HPCE apparatus 10 includes a light-tight container 11' that may be fabricated from any suitable material such as plexiglass. The container 11' is configured to receive therein the insulated holder 100. The container 11' insulates the operator and module 26' from high voltages. The container 11' also minimizes stray light that may affect detection results. The container 11' also serves as a support for the insulated holder 100, the buffer reservoirs 16', 16', the electrical connections to the power supply PS, the external heat sink plates 34' if utilized, and the radiation coupling means 80.

Figures 13, 14:
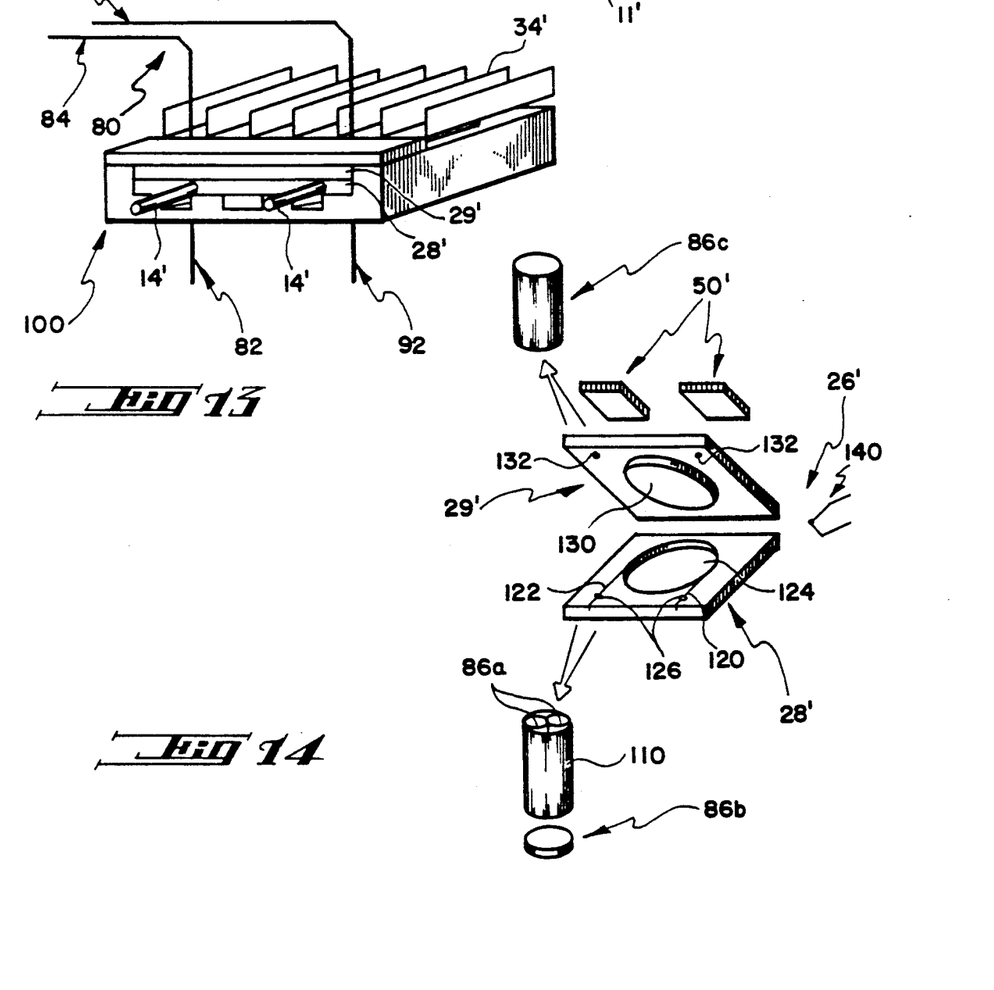
FIG. 13 is a perspective view of a portion of the electrophoretic apparatus of FIG. 12.
FIG. 14 is an exploded perspective view of the integrated temperature control/alignment module of FIG. 13.

The holder 100, see FIG. 13, is formed from an electrically insulative material and is configured so that the integrated temperature control/alignment module 26' may be slidably inserted therein or withdrawn therefrom. Other features of the holder 100 are described in conjunction with other elements in further detail hereinbelow.

The radiation coupling means 80 includes source fiber optics 82 mounted in the holder 100 as shown in FIG. 13 and operative to transmit UV radiation from the radiation source to the integrated temperature control/alignment module 26'. The radiation coupling means 80 further includes sample cell fiber optics 84 mounted in the holder 100 in registration with the source fiber optics 82 and operative to transmit radiation from the module 26' to the detection means 24'.

Sample optical coupling means 86 as exemplarily illustrated in FIG. 14 may be mounted in combination with the integrated temperature control/alignment module 26' to couple radiation from the source fiber optics 82 onto the capillary column 12 and to couple radiation exiting the capillary column 12' to the sample cell fiber optics 84. In one preferred embodiment illustrated in FIG. 14, the sample optical coupling means 86 comprises two 100 micron optical fibers 86a, a fused silica lens 86b, and one 600 micron optical fiber 86c. In another preferred embodiment, the sample optical coupling means 86 comprises a first 600 micron optical fiber 86a, a fused silica lens 86b, and a second 600 micron optical fiber 86c.

The two optical fibers 86a, having lengths of about 30, are secured together with cyanoacrylate glue, polished and press-fitted into a teflon tube 110 mounted in the first mounting block member 28'. First ends of the fibers 86a optically interface with the fused silica lens 86b that focuses radiation from the source fiber optics 82 into the fibers 86a. Signal losses for the fiber optics 86a above 220 nm are about 1.0 db/m, i.e., greater than 80% transmittance. The use of two optical fibers improves the signal to noise ratio. For this preferred embodiment, a capillary window 13' having an axial length of about 240 micrometers is formed in the capillary column 12'.

The 600 micrometer optical fiber 86c is press-fitted into the second mounting block member 29'. The 600 micrometer optical fiber 86c optically couples radiation exiting the capillary column 12' into the sample cell fiber optics 84.

The HPCE apparatus 10 may also include reference radiation coupling means 90 comprising first and second reference cell fiber optics 92, 94 and reference optical coupling means 96. The reference cell fiber optics 92, 94 are mounted in registration in the holder 100 and operative to couple radiation between the on-column detection device 22', 24' and the integrated temperature control/alignment module 26'. The reference optical coupling means 96, which may be similar to that described in the preceding paragraphs, is disposed in combination with the integrated temperature control/alignment module 26' to couple radiation from the first reference cell fiber optics 92 onto the capillary column 12' and to couple radiation exiting the capillary column 12' to the second reference cell fiber optics 94.

The reference radiation coupling means 90 may be utilized to generate an electropherogram of the injected analyte. This permits a quantitative determination of how much analyte has been injected into the capillary column 12'. The above-described configuration provides optical decoupling between the fiber optics mounted in the holder 100 and the optical coupling means disposed in combination with the integrated temperature control/alignment module 26'.

The complementary mounting plate members 28', 29' are fabricated from a material that has a high thermal conductivity and good electrical insulating characteristics. Alumina, $Al_2O_3$, which has a thermal conductivity of about 36 W $m^{-1}$ $°K^{-1}$, is one material having utility for fabricating the mounting plates 28', 29'. Boron nitride, Bn, which has a thermal conductivity of about 56 W $m^{-1}$ $°K^{-1}$, is another material having utility for fabricating the mounting plates 28', 29'. Bn, in addition to having a higher thermal conductivity, also is easier to machine than $Al_2O_3$, thereby reducing fabrication costs. The high thermal conductivity of the plates 28', 29' provides the solid state cooling capacity that maintains the outer surface of substantially the entire length of the capillary column 12' at the predetermined electrophoretic operating temperature $T_{cc}$.

The plates 28', 29' are configured to be mated in combination and the combination is dimensioned to be slidably received in the holder 100. The thermal conductivity between the mated plates 28', 29' may be enhanced by spreading ethylene glycol on the abutting surfaces of the plates 28', 29' prior to mating. The plates 28', 29' are machined to provide good thermal contact with and to seat and lock the capillary column 12' within the module 26'. With the plates 28', 29' mated in combination with the capillary column 12 mounted therein and the ends 14', 14' thereof disposed in reservoirs 16', 16' such as 0.5 mL micro test tubes, only about 0.5 cm of each end 14' of the capillary column 12' is exposed between the reservoir 16' and the integrated temperature control/alignment module 26' when mounted in the holder 100. The minimal length of exposed capillary column minimizes temperature deviations within the capillary column due to Joule heating.

The first mounting plate 28' includes first and second capillary support grooves 120, 122 and a well 124 to support capillary columns of different lengths therein. The capillary support grooves 120, 122 are dimensioned for snugly mounting the respective ends of a given capillary column. Ports 126, as required, are formed in the respective support grooves 120, 122 and extending through the plate 28' for receiving corresponding elements of the sample and reference optical coupling means as described hereinabove. In one preferred embodiment, exemplarily illustrated in FIG. 15., a thin (about one ten-thousandth of an inch thick) stainless steel mounting member 125 is disposed in the plate 28' about the port 126 defining the detection zone. The mounting member 125 includes a capillary mounting groove 125a and a slit 125b.

Figure 15:
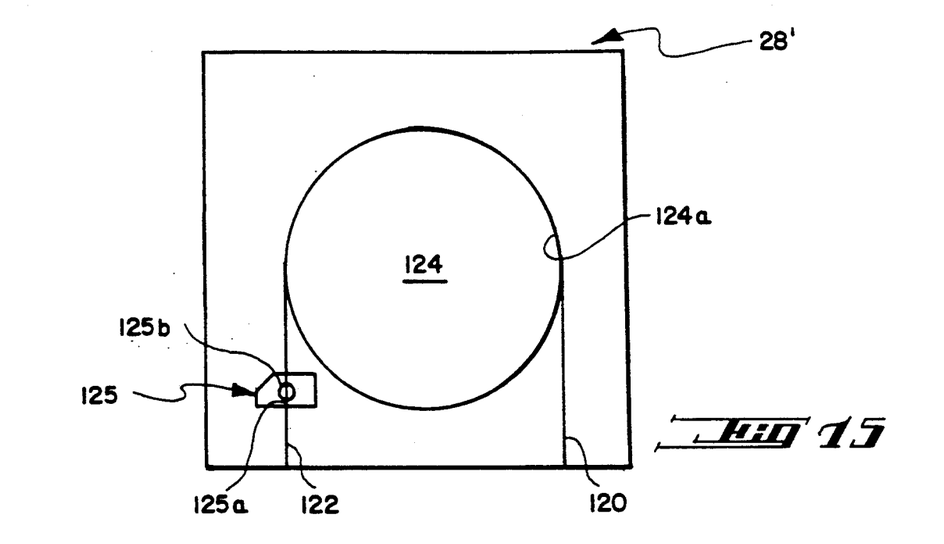
FIG. 15 is a plan view of one plate of the module shown in FIG. 14.

In one preferred embodiment, the capillary support grooves 120, 122 are dimensioned for mounting a capillary column 12' having an O.D. of about 357 micrometers. The I.D. of the capillary column 12' is selectively variable, e.g., 50, 100 or 200 micrometers, depending upon the particular application.

The well 124 of the first mounting plate 28' is defined by a circumferential wall 124a having a predetermined circumference. Polyimide coated capillary columns have sufficient resiliency such that the intermediate portion of the mounted column 12' abuts against the circumferential wall 124a. The intermediate portion of any particular capillary column may be coiled a predetermined number of turns within the well 124 so that the capillary column 12' mounted within the integrated temperature control/alignment module 26' has a predetermined working length. The predetermined working length is determined by the number of turns of the intermediate portion of the capillary column and the predetermined circumference of the well 124.

The basic configuration of the integrated temperature control/alignment module 26' embodiment, i.e., the well 124, permits capillary columns of different lengths to be mounted therein while concomitantly providing the same degree of solid state cooling, temperature control, therefor. Thus, the integrated temperature control/alignment module 26' may be utilized for the electrophoretic separation of a variety of analytes and with gel or open columns.

In one preferred embodiment, the well 124 has a predetermined circumference such that capillary columns of different lengths may be coiled therein to provide column working lengths of 15, 30, 45 or 60 centimeters, respectively. Column working lengths of 45 and 60 centimeters are typically used in electrophoretic separations.

The second mounting plate member 29' is formed to complement the first mounting plate 28' and includes a plug 130 and ports 132. The plug 130 is configured to be disposed within the well 124 to retain the intermediate portion of the capillary column 12' in abutting relation against the circumferential wall 124a. The plug 130 may be configured so that a predetermined gap, e.g., about 400 microns, exists between the periphery of the plug 130 and the circumferential wall 124a so that the capillary column 12' may be coated with a high temperature thermally conductive paste or ethylene glycol to enhance thermal contact between the column 12' and the integrated temperature control/alignment module 26'.

The ports 132 are formed to extend through the second mounting plate 29' in registration with the ports 126 of the first mounting plate 28'. The ports 132 are configured to receive corresponding elements of the sample and reference optical coupling means as described hereinabove.

Figure 16:
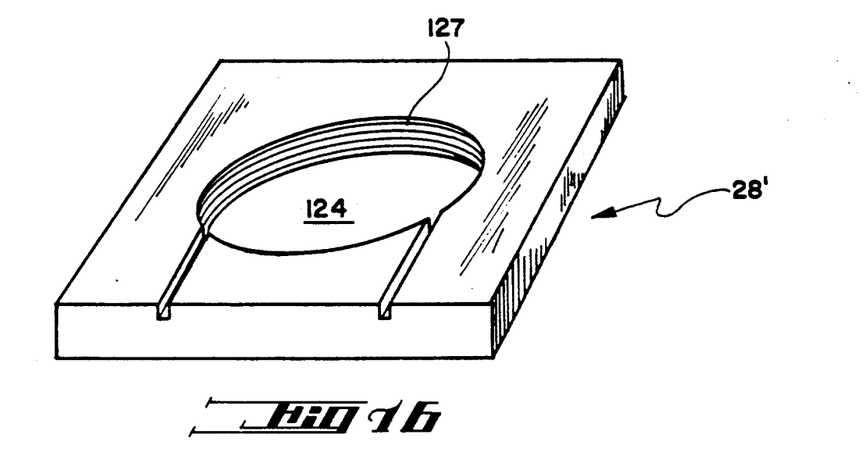
FIGS. 16 and 17 illustrate another embodiment of the module of FIG. 14.
Figure 17:
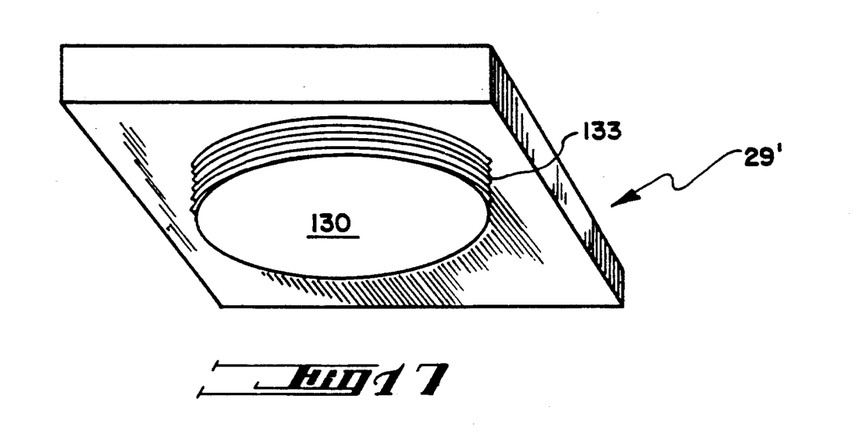

Alternative embodiments for the first and second mounting block members 28', 29' are illustrated in FIGS. 16 and 17. Grooves 127 may be formed in the circumferential wall 124a to receive the intermediate portion of the capillary column. Grooves 133 may be formed in the sidewall of the plug 130 to receive the intermediate portion of the capillary column.

The holder 100 is configured so that a temperature measuring means 140 such as a thermistor, thermocouple or RTD may be thermally coupled to the integrated temperature control/alignment module 26' to monitor the predetermined electrophoretic operating temperature $T_{cc}$ of the capillary column. The first and second mounting plates 28', 29' may be further configured so that the temperature measuring means 140 may be disposed in direct thermal contact with the capillary column 12'. The temperature measuring means 140 is electrically coupled to the thermoelectric temperature controller 60' to provide temperature feedback signals thereto to facilitate temperature control of the capillary column. The use of the temperature measuring means 140 enhances the stability of the solid state temperature control system by providing proportional current control. Feedback signals from the temperature measuring means 140 is fed to the controller 60' to regulate the current flow to the thermopiles 50'. This, in turn, regulates the heat transfer rate between the module 26' and the mounted capillary column 12'.

In another embodiment of the present invention, the hereinabove-described device may be utilized with an off-line detector such as a mass spectrometer or an electrochemical detector In this embodiment, the primary function of the integrated temperature control/alignment module 26' is to provide thermoelectric temperature control for the capillary column to maintain same at the predetermined electrophoretic operating temperature $T_{cc}$. The integrated temperature control/alignment module 26' is operative for mounting the capillary column 12' and, in addition, serves to align the capillary column 12' in the sense that capillary column 12' is centered within the module 26', i.e., that is, to ensure that the ends 14', 14' of the capillary column evenly extend outwardly from the module 26'.

Other embodiments and variations of the present invention are possible in light of the above teachings. It is therefore to be understood that within the scope of the appended claims, the present invention may be practiced otherwise than as specifically described hereinabove.

What is claimed is:

1. An integrated temperature control/alignment system for high performance capillary electrophoresis, comprising:

means for thermoelectrically regulating heat transfer between the capillary column and the ambient environment to maintain the capillary column at a predetermined electrophoretic operating temperature; and means for mounting the capillary column in a predetermined position as part of a capillary electrophoretic apparatus, said mounting means being formed from an electrically insulative, high thermally conductive material and configured to envelope the capillary column over substantially the entire working length thereof to provide efficient heat transfer between the capillary column and said mounting means to maintain the capillary column at said predetermined electrophoretic operating temperature, and wherein said thermoelectric regulating means is disposed in thermal contact with said mounting means, said mounting means including means for physically engaging respective ends of the capillary column to lock the capillary column in said predetermined position within said mounting means, and means for disposing the intermediate portion of the capillary column within said mounting means in thermal contact therewith, said disposing means being configured to accommodate the intermediate portion of capillary columns of varying lengths wherein the working length of the capillary column may be varied in predetermined increments for different electrophoretic separations.

2. An integrated temperature control/alignment system for use with a high performance capillary electrophoretic apparatus including a capillary column, a power supply, a thermoelectric controller, a detection device for on-column detection, and means for coupling radiation between the detection device and said integrated temperature control/alignment system, comprising:

means for thermoelectrically regulating heat transfer between the capillary column and the ambient environment to maintain the capillary column at a predetermined electrophoretic operating temperature; and means for mounting the capillary column as part of the capillary electrophoretic apparatus, said mounting means being formed from an electrically insulative, high thermally conductive material and configured to envelope the capillary column over substantially the entire working length thereof to provide efficient heat transfer between the capillary column and said mounting means to maintain the capillary column at said predetermined electrophoretic operating temperature, and wherein said thermoelectric regulating means is disposed in thermal contact with said mounting means, said mounting means including means for aligning the capillary column within said mounting means in a predetermined position to the radiation coupling means to provide on-column detection, said aligning means including means for optically coupling radiation from the radiation coupling means onto the capillary column and for optically coupling radiation from the capillary column to the radiation coupling means, means for physically engaging respective ends of the capillary column to lock the capillary column in said predetermined position within said mounting means, and means for disposing the intermediate portion of the capillary column within said mounting means in thermal contact therewith, said disposing means being configured to accommodate the intermediate portion of capillary columns of varying lengths wherein the working length of the capillary column may be varied in predetermined increments for different electrophoretic separations.

3. The integrated temperature control/alignment system of claim 2 wherein said mounting means further comprises first and second mounting plates having a complementary configuration wherein said first and second mounting plates mated in combination form an integrated temperature control/alignment module.

4. The integrated temperature control/alignment system of claim 3 wherein said first mounting plate includes a well defined by a circumferential wall having a predetermined circumference and first and second grooves contiguous with said well and extending to one edge of said first mounting plate, and further wherein said second mounting plate includes a plug having a configuration wherein said plug is disposed within said well with said first and second mounting plates mated in combination such that said well and said plug are in thermal contact with the intermediate portion of the capillary column, said well comprising said disposing means wherein said predetermined circumference of said circumferential wall defines said predetermined increments, and said first and second grooves comprising said means for physically engaging respective ends of the capillary column.

5. The integrated temperature control/alignment system of claim 4 wherein said circumferential wall includes grooves having a configuration to accommodate the intermediate portion of the capillary column.

6. The integrated temperature control/alignment system of claim 4 wherein said plug includes grooves having a configuration to accommodate the intermediate portion of the capillary column.

7. The integrated temperature control/alignment system of claim 4 wherein said first mounting plate includes a first port formed in one of said first and second grooves and extending through said first mounting plate, and further wherein said second mounting plate includes a first port extending therethrough in registration with said first port of said first mounting plate, said first ports of said first and second mounting plates being configured for mounting said optical coupling means to provide on-column sample detection of electrophoretic separation in the capillary column.

8. The integrated temperature control/alignment system of claim 7 wherein said optical coupling means comprises:

at least one optical fiber mounted in said first port of said first mounting plate;

a lens mounted in said first port of said first mounting plate and operative to focus radiation from the radiation coupling means onto said at least one optical fiber; and an optical fiber mounted in said first port of said second mounting plate.

9. The integrated temperature control/alignment system of claim 7 wherein said first mounting plate further includes a second port formed in the other of said first and second grooves and extending through said first mounting plate, and further wherein said second mounting plate includes a second port extending therethrough in registration with said second port of said first mounting plate, said second ports of said first and second mounting plates being configured for mounting said optical coupling means to provide on-column reference detection of analyte injected into the capillary.

10. The integrated temperature control/alignment system of claim 2 further comprising means for monitoring said predetermined electrophoretic operating temperature of the capillary column, said monitoring means being disposed in thermal contact with said mounting means, said temperature monitoring means being electronically interfaced with the thermoelectric controller to provide temperature signals thereto wherein the thermoelectric controller provides proportional temperature control for said thermoelectric regulating means to maintain the capillary column at said predetermined electrophoretic operating temperature.

11. The integrated temperature control/alignment system of claim 2 further comprising means for monitoring said predetermined electrophoretic operating temperature of the capillary column, said monitoring means being disposed in direct thermal contact with the capillary column, said temperature monitoring means being electronically interfaced with the thermoelectric controller to provide temperature signals thereto wherein the thermoelectric controller provides proportional temperature control for said thermoelectric regulating means to maintain the capillary column at said predetermined electrophoretic operating temperature.

* * * * *

UNITED STATES PATENT AND TRADEMARK OFFICE
CERTIFICATE OF CORRECTION

PATENT NO. : 5,085,757
DATED : February 4, 1992
INVENTOR(S) : Barry L. Karger, et al.

It is certified that error appears in the above-identified patent and that said Letters Patent is hereby corrected as shown below:

Column 2, line 40, "column FIG. 18" should read --column. FIG. 18--.

Column 14, line 58, "column 12 to" should read --column 12' to--.

Column 15, line 1, "thermopiles 50" should read --thermopiles 50'--.

Column 15, line 37, "column 12" should read --column 12'--.

Column 15, line 48, "30, are" should read --30 cm, are--.

Column 16, line 46, "column 12" should read --column 12'--.

Signed and Sealed this

Second Day of November, 1993

Attest:

BRUCE LEHMAN

*Attesting Officer*   Commissioner of Patents and Trademarks